(12) United States Patent
Lavania et al.

(10) Patent No.: US 11,460,643 B2
(45) Date of Patent: Oct. 4, 2022

(54) GUARDING WALL MECHANISM FOR HOUSING AN OPTICAL FIBER

(71) Applicants: Anupam Lavania, Gujarat (IN); Shilpa Malik, Gujarat (IN)

(72) Inventors: Anupam Lavania, Gujarat (IN); Shilpa Malik, Gujarat (IN)

( * ) Notice: Subject to any disclaimer, the term of this patent is extended or adjusted under 35 U.S.C. 154(b) by 0 days.

(21) Appl. No.: 17/297,368

(22) PCT Filed: Nov. 26, 2019

(86) PCT No.: PCT/IB2019/060148
§ 371 (c)(1),
(2) Date: May 26, 2021

(87) PCT Pub. No.: WO2020/109981
PCT Pub. Date: Jun. 4, 2020

(65) Prior Publication Data
US 2022/0035101 A1 Feb. 3, 2022

(30) Foreign Application Priority Data
Nov. 26, 2018 (IN) .............................. 201821044486

(51) Int. Cl.
*G02B 6/36* (2006.01)
*A61B 5/00* (2006.01)

(52) U.S. Cl.
CPC .......... *G02B 6/3624* (2013.01); *A61B 5/0059* (2013.01); *A61B 5/6834* (2013.01)

(58) Field of Classification Search
CPC ....................... G01N 2021/4742; G02B 6/3624
See application file for complete search history.

(56) References Cited

U.S. PATENT DOCUMENTS 4,718,406 A * 1/1988 Bregman ................. A61B 1/07
600/113
2018/0169432 A1 6/2018 Nishimura et al.

OTHER PUBLICATIONS

International Search Report and Written Opinion, International Patent Application No. PCT/IB2019/060148, dated Jun. 1, 2020 (8 pages).
International Preliminary Report on Patentability, International Patent Application No. PCT/IB2019/060148, dated Oct. 9, 2020 (4 pages).

* cited by examiner

*Primary Examiner* — Omar R Rojas
(74) *Attorney, Agent, or Firm* — Hamre, Schumann, Mueller & Larson, P.C.

(57) ABSTRACT

The present disclosure discloses a guarding wall mechanism (100) for an optical fiber (101). The mechanism (100) comprises a housing (202) adapted to house the optical fiber (101), wherein the housing (202) defines a space (108) between the optical fiber (101) and a guarding wall of the housing (202). A plurality of suction units (103) disposed in the space (108). Each of the plurality of suction units (103) are configured to selectively exert suction pressure on an examination surface in contact with a free end (109) of the optical fiber (101). The guarding wall mechanism (100) of the present disclosure eliminates leakage of light and reduces Fresnel losses. Also, the mechanism (100) improves comfort to the patient during examination.

16 Claims, 5 Drawing Sheets

GUARDING WALL MECHANISM FOR HOUSING AN OPTICAL FIBER

TECHNICAL FIELD

The present disclosure generally relates to the field of optical devices. Particularly but not exclusively, the present disclosure relates to those optical devices that need to be brought in contact against a surface of a subject for investigation, therapeutic or curing purpose. Further embodiments of the disclosure disclose a mechanism for guiding or supporting an optical fiber on an examination surface.

BACKGROUND

Spectroscopy is a study of light matter interaction measured through the changes in the properties of the light before and after its interaction with the matter, matter being solid, liquid or gas. It may be frequently employed in qualitative and quantitative analysis of materials, wherein scattered beam or radiation may be collected and analyzed.

Spectroscopy may be broadly classified into two categories—contact type spectroscopy and a non-contact type spectroscopy. In the contact type spectroscopy, when the source and detector are placed at a distance from each other, the light may incident via the optical fiber system. Then the system may be placed over the examination site. Further, the source emits a wave through the examination site and this wave gets reflected and received by the detector. The detector provides the required output through the detected signal. In the non-contact type spectroscopy, the direct contact of the examination site with the source is eliminated. The source and the examination site will not have any physical contact during the examination process or before the examination process Yet another classification of spectroscopy may be X-ray spectroscopy, flame spectroscopy, atomic emission spectroscopy, atomic absorption spectroscopy, spark or arc spectroscopy, visible or ultraviolet spectroscopy, infrared (IR) and near infrared (NIR) spectroscopy. Particularly, the infrared (IR) spectroscopy relies on the fact that molecules absorb specific frequencies which is determined by the mass of the atoms, wherein the near infrared (NIR) shows a greater penetration depth into a sample than mid-infrared radiation. it allows large samples to be measured in each scan by NIR spectroscopy. The NIR spectroscopy has numerous practical applications that include medical diagnosis, pharmaceuticals, biotechnology, various analysis and chemical imaging of intact organisms.

Generally, there may be some challenges encountered with the NIR based contact spectroscopy, and such challenges may include difficulty to create an efficient, stable and comfortable optical interference with the sample surface, for example, scalp, especially in the presence of hair. Hair and hair follicles may act as strong attenuators leading to poor signal quality. Often, significant time and effort has to be invested to ensure that a minimum amount of hair or no hair remains under the probe.

Further, diffuse reflectance spectroscopy system may be used for examining the surface of sample. The diffuse reflectance spectroscopy system includes probes with a plurality of source for emitting radiation of desired frequencies on the sample to be tested and plurality of detectors for receiving sample altered radiations. The radiation received by the detectors may be analyzed to determine the characteristics of the sample. The diffuse reflectance spectroscopy system may be optical fiber based system. In such a case, there may be two kinds of optical fiber systems that may be employed in diffuse reflectance spectroscopy. The existing optical fiber system consists of a bare fiber ends where the fibers come directly in contact with the surface of a skin or a material depending on the application. Although, the bare fiber may be able to come in contact with the most remote places of the sample surface such as skin or any other material to be tested, these bare fiber ends are not robust, since pressure applied on the fibers may break them due to the brittle nature of the fibers. Secondly, these bare fibers may be aligned at a random angle during each measurement, which may render the data collected inconsistent. Also, the bare fibers when pressed against the skin of a subject, it may cause discomfort to the subject.

In yet another kind of optical fiber system, a fiber bundle may be used to collect more signals thereby increasing the signal to noise ratio but if these fibers are also bare at the termination end, they will suffer from the same challenges as single bare fiber. which are less susceptible to damage that may be caused to the optical fibers when excessive pressure is applied on them during application. Also the multiple fiber system can detect more signals and is robust compared to the bare fiber system. However, such fiber bundle cannot come in contact with the remote places of the sample or the examination site. Additionally, these type of optical fiber systems are known to create air pockets between the fiber tip and the surface of the skin or material, especially when the surface is curved.

In conventional mechanism hair or any such material acts as a barrier between face of the optical fiber and the surface. This happens when the outer diameter of the optical fiber is not small enough to make contact with the skin in between hair follicles. Hence the detected signal intensity may reduce significantly and may produce low sound to noise ratio and unpredictability in the output signal.

The present disclosure is directed to overcome one or more limitations stated above or similar limitations associated with the conventional mechanisms.

SUMMARY

The shortcomings of the conventional mechanisms are overcome, and additional advantages are provided through the provision of mechanism as disclosed in the present disclosure.

Additional features and advantages are realized through the techniques of the present disclosure. Other embodiments and aspects of the disclosure are described in detail herein and are considered a part of the disclosure.

In one non-limiting embodiment of the disclosure, a guarding wall mechanism for an optical fiber is disclosed. The mechanism comprises a housing adapted to house the optical fiber, wherein the housing defines a space between the optical fiber and a guarding wall of the housing. A plurality of suction units disposed in the space. Each of the plurality of suction units are configured to selectively exert suction pressure on an examination surface in contact with a free end of the optical fiber.

In an embodiment of the disclosure, the housing is a hollow tube comprising an inner wall and an outer wall. The housing is made of polymeric material.

In an embodiment of the disclosure, an end of the housing proximal to the free end of the at least one optical fiber is defined with a chamfer.

In an embodiment of the disclosure, the chamfer extends radially inward from the inner wall of the housing towards a substantially central portion of the housing up to a predetermined length and defining an opening at the substantially central portion of the housing.

In an embodiment of the disclosure, a flange portion is defined around the opening, wherein the flange portion is configured to support the free end of the optical fiber.

In an embodiment of the disclosure, each of the plurality suction units comprises a suction tube extending from a cavity defined by the chamfer and a suction bulb at a free end of the suction tube.

In an embodiment of the disclosure, a plurality of reflective plates are provisioned within the suction units, wherein the plurality of reflective plates are configured to reflect light entering the plurality of suction units.

In an embodiment of the disclosure, each of the plurality of suction units are coupled to an actuator.

In an embodiment of the disclosure, the actuator is communicatively coupled to the control unit and the control unit is configured to selectively operate the actuator to activate and deactivate the plurality of suction units.

In an embodiment of the disclosure, the optical fiber housed within the housing is at least one of a transmitter optical fiber and a receiver optical fiber.

In an embodiment of the disclosure, the optical fiber housing includes at least a connector portion, a body portion and a ferrule.

In an embodiment of the disclosure, the connector portion is configured to facilitate transmission of light between at least one of a light source, a detector and the ferrule.

In an embodiment of the disclosure, the body of the optical fiber is configured to connect the ferrule of the optical fiber to the connector of the optical fiber and the body portion is made of at least one of a flexible material and a solid material.

In an embodiment of the disclosure, the ferrule includes the free end of the optical fiber and the ferrule is configured to support the free end of the optical fiber.

In another non-limiting embodiment of the disclosure, an optical system for examining a surface of a subject is disclosed. The optical system comprises at least one optical fiber. The optical fiber comprises a ferrule including a free end of the optical fiber. The optical fiber comprises a connector portion configured to facilitate transmission of light between at least one of a light source, a detector and a ferrule. Optical fiber comprises a body, wherein one end of the body is coupled to the ferrule and another end of the body is coupled to the connector. A core of the optical fiber extends throughout the ferrule, body portion and the connector portion, wherein the core of the optical fiber is configured to transmit the light from the source to the examination surface.

A guarding wall mechanism for the at least one optical fiber. The guarding wall mechanism includes a housing adapted to house at least one optical fiber, wherein the housing defines a space between the optical fiber and a guarding wall of the housing. A plurality of suction units disposed in the hollow space, wherein each of the plurality of suction units are configured to selectively exert suction pressure on an examination surface to bring the examination surface in contact with a free end of the optical fiber.

It is to be understood that the aspects and embodiments of the disclosure described above may be used in any combination with each other. Several of the aspects and embodiments may be combined together to form a further embodiment of the disclosure.

The foregoing summary is illustrative only and is not intended to be in any way limiting. In addition to the illustrative aspects, embodiments, and features described above, further aspects, embodiments, and features will become apparent by reference to the drawings and the following description.

BRIEF DESCRIPTION OF THE ACCOMPANYING FIGURES

The above-mentioned aspects, other features and advantages of the disclosure will be better understood and will become more apparent by referring to the exemplary embodiments of the disclosure, as illustrated in the accompanying drawings.

The figures depict embodiments of the disclosure for purposes of illustration only. One skilled in the art will readily recognize from the following description that alternative embodiments of the mechanism illustrated herein may be employed without departing from the principles of the disclosure described herein.

DETAILED DESCRIPTION

The foregoing has broadly outlined the features and technical advantages of the present disclosure in order that the description of the disclosure that follows may be better understood. Additional features and advantages of the disclosure will be described hereinafter which form the subject of the disclosure.

It should be appreciated by those skilled in the art that the conception and specific embodiment disclosed may be readily utilized as a basis for modifying or designing other devices for carrying out the same purposes of the present disclosure. It should also be realized by those skilled in the art that such equivalent constructions do not depart from the spirit and scope of the disclosure. The novel features which are believed to be characteristic of the disclosure, as to its organization, together with further objects and advantages will be better understood from the following description when considered in connection with the accompanying figures. It is to be expressly understood, however, that each of the figures is provided for the purpose of illustration and description only and is not intended as a definition of the limits of the present disclosure. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Embodiments of the present disclosure disclose a guarding wall mechanism for an optical fiber. The guarding wall mechanism of the present disclosure ensures that a free end of the optical fiber is protected from any possible damage that may be caused due to uneven application of pressure on the probes. Also, with the provision of the guarding wall mechanism for the optical fiber, there may be reduction in Fresnel losses and light leakage. Further, with the guarding wall mechanism of the present disclosure, air pockets that may be caused between the examination surface and the free end of the optical fiber are significantly reduced.

The guarding wall mechanism for an optical fiber according to embodiments of the present disclosure may include a housing adapted to house the optical fiber. In an embodiment, the optical fiber housed within the housing may be at least one of a transmitter optical fiber and/or a receiver optical fiber. The optical fiber may include a connector portion, a body portion and a ferrule. The connector portion of the optical fiber may be configured to transmit light efficiently between a light source or detector and the ferrule. The connector portion may be configured to connect the body portion of the optical fiber to the ferrule of the optical fiber. In an embodiment, the body of the optical fiber may be made of a flexible material. In an embodiment, the ferrule portion may include free ends of the optical fiber and the ferrule may be configured to support the free end of the optical fiber. In an embodiment, the optical fiber includes a core extending throughout the ferrule, the body portion and the connector portion. The core may be configured to transmit the light from the source to the free end of the optical fiber.

Further, the housing defines a space between the optical fiber and guarding wall of the housing. In an embodiment, the housing may be made of a polymeric material. In an exemplary embodiment, the polymeric material used may be a hard plastic. The guarding wall mechanism includes a plurality of suction units disposed in the space defined in the housing. In another embodiment, each of the plurality of suction units are configured to selectively exert suction pressure on the examination surface. The said suction pressure exerted by the suction units aid in bringing the examination surface in contact (or much closer) with the free end of the optical fiber.

Further, an end of the housing of the guarding wall mechanism proximal to the free end of the at least one optical fiber may be defined with a chamfer. In an embodiment, the chamfer extends inwardly from the inner wall of the housing towards a substantially central portion of the housing. The chamfer may extend up to a predetermined length and thus defining an opening at the substantially central portion of the housing. Further, a flange portion may be defined around the opening at the substantially central portion around the chamfer. The said flange defined around the chamfer is configured to support the free end of the optical fiber.

In an embodiment, the suction units includes a suction tube extending from a cavity defined by the chamfer and a suction bulb may be provided at the free end of the suction tube. In an embodiment, the suction units may be coupled to actuators and the actuators may be further coupled to a control unit. The control unit coupled to the actuators may be configured to selectively operate the actuator to activate and deactivate the plurality of suction units. In an embodiment, the suction units include a plurality of reflective plates positioned within the suction tubes. The said plurality of reflective plates may reflect light entering the plurality of suction units. In an embodiment, the reflective plates may be sized to cover only a part (say half) of the aperture of the suction tube. The said suction tubes are placed alternately on opposite sides of the suction tube in a configuration so as to cover the entire aperture or inner cross sectional area of the tube.

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described below. It should be understood, however that it is not intended to limit the disclosure to the particular forms disclosed, but on the contrary, the disclosure is to cover all modifications, equivalents, and alternative falling within the spirit and the scope of the disclosure.

The terms "comprises", "comprising", or any other variations thereof, are intended to cover a non-exclusive inclusion, such that a mechanism that comprises a list of components does not include only those components but may include other components not expressly listed or inherent to such mechanism. In other words, one or more elements in the device or mechanism proceeded by "comprises . . . a" does not, without more constraints, preclude the existence of other elements or additional elements in the mechanism.

In the following detailed description of the embodiments of the disclosure, reference is made to the accompanying figures that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

Figure 1:
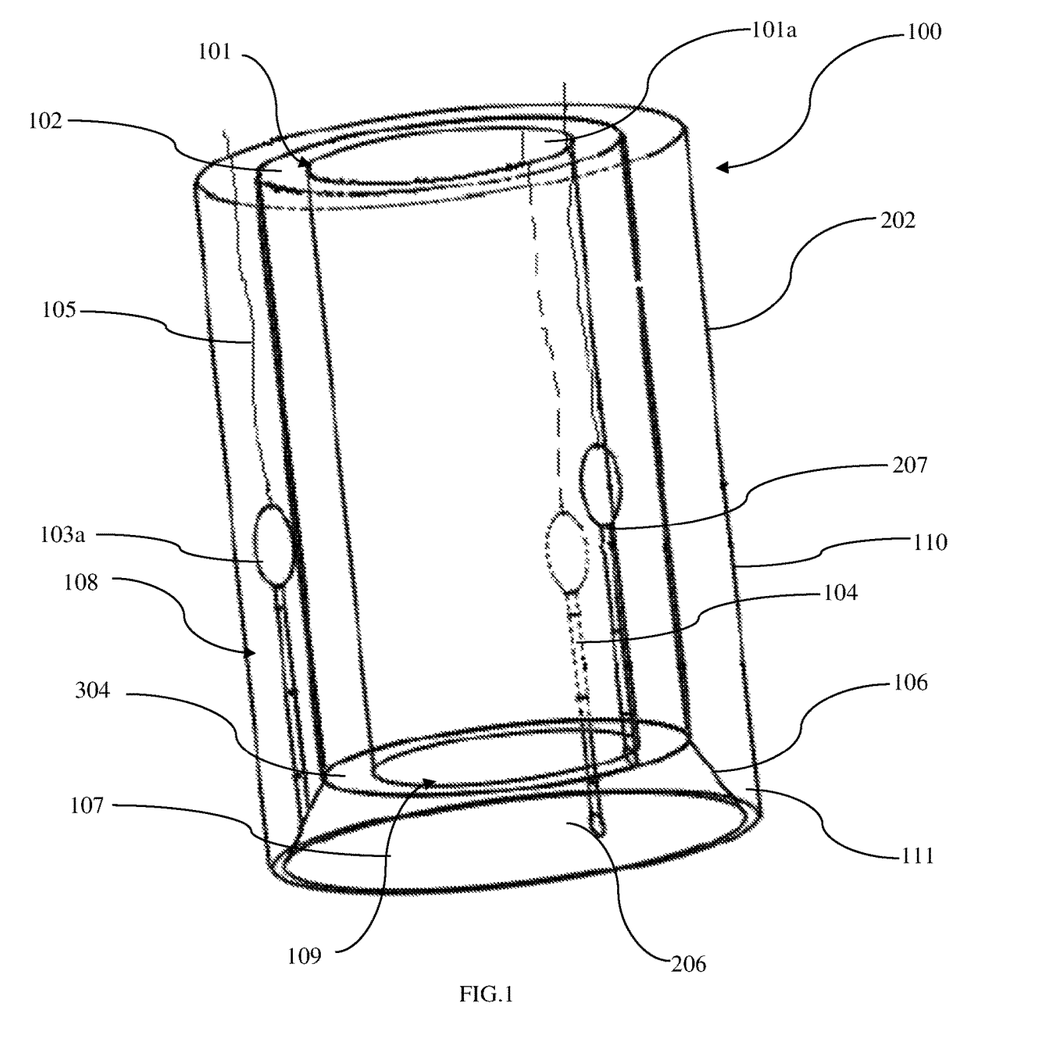
FIG. 1 illustrates a perspective view of a guarding wall mechanism for housing an optical fiber, in accordance with an embodiment of the disclosure.

FIG. 1 is an exemplary embodiment of the present disclosure depicting a guarding wall mechanism (100) for housing or protecting an optical component such as optical fiber (101). Optical fibers (101) may generally be used for examination of a sample surface (200) [shown in FIG. 2B].

The optical fiber (101) may come in contact with the sample surface (200) during examination. However during usage of the optical fiber (101), there may be possibilities of user applying additional force or pressure on the optical fiber (101) which may cause damage to the optical fiber (101). Thus, the present disclosure discloses a guarding wall mechanism (100) for limiting the damage caused to the optical fiber (101) and thus safeguard it.

As shown in FIG. 1, the guarding wall mechanism (100) consists of a housing (202) configured to house and support the optical fiber (101). A space (108) may be defined between the optical fiber (101) and the housing (202) upon positioning the optical fiber (101) within the housing (202). In an embodiment, each optical fiber (101) includes a cladding (102) which acts as a protective covering for the side walls of the optical fiber (101). In an embodiment, the housing (202) may be a hollow tube which is open at one end to allow optical fibers (101) to be ingressed, egressed and house the optical fibers (101). In an embodiment, an end of the housing (202) proximal to a free end (109) of the optical fiber (101) may be chamfered (106), such that it comes in contact with outer surface of the cladding (102). In an embodiment of the disclosure, the chamfer (106) may extend radially inward from an inner wall (111) of the housing (202) towards a substantially central portion of the housing (202) up to a predetermined length and defining an opening at the substantially central portion of the housing (202). A flange (304) may be defined around the opening, wherein the flange (304) may aid in supporting the optical fiber (101) at a predetermined distance from the examination surface. The chamfer (106) provided in the housing (202) may aid in natural upliftment of the surface of the sample into the cavity (107) to some extent. For example, if the sample surface is considered to be skin, when the guarding wall mechanism (100) is placed on the surface on the skin, due to the chamfer (106) angle provided at the bottom of the housing (202) the skin may be uplifted into the cavity (107) of the guarding wall mechanism (100).

In an embodiment of the disclosure, the housing (202) may be configured to house the optical fibers (101), wherein the optical fibers (101) are either placed in the housing (202) of the guarding wall mechanism (100) or it may be affixed to the housing (202) of the guarding wall mechanism (100), thereby providing a rigid support to the optical fiber (101) structure. In an embodiment, the optical fiber (101) may be affixed through means such as but not limited to adhesives.

Further, as shown in FIG. 1, the mechanism (100) includes a plurality of suction units (103) which further includes a suction bulb (103) and a suction tube (104). The suction units (103) present in the guarding wall (100) are used to further uplift the sample surface (200) to ensure contact with the optical fibers (101). In an embodiment of the present disclosure, the suction units (103) may be coupled to an actuator to activate the suction units (103). In another embodiment, actuators [not shown] may be configured to activate and deactivate the suction units (103) and may hereinafter be referred to as activating and deactivating actuators. The activating and deactivating actuators may be provided for the functioning of the suction units (103). The activation and deactivation actuators may be at least one of but not limiting to magnetic, mechanical, electronic/electrical, pneumatic or hydraulic means. In an embodiment, the actuator may be coupled to a control unit (105). The control unit (105) may selectively activate or deactivate the suction units (103). In an embodiment, the control unit (105) may activate the suction bulbs (103) present in the suction units (103) i.e., they may be compressed to remove air from the suction bulb (103) before placing the guarding wall mechanism (100) on the surface of the sample through the activation actuator. Once mechanism (100) is placed over the sample surface (200), the control unit (105) may deactivate the suction bulbs (103). The suction bulbs (103) may be released through the deactivation actuators which creates a low pressure inside the suction bulb (103). Due to the low pressure created inside the suction bulb (103), the high pressure air present in the cavity (107) may flow into the suction bulb (103) thereby creating vacuum. Due to the movement of air from high pressure region in cavity (107) to the low pressure region in suction bulbs (103), a suction may be created which may lead to the sample surface (200) being uplifted. The surface may then come in contact with a free end (109) of the optical fibers (101). In an embodiment of the present disclosure, the plurality of suction units (103) provided for the upliftment or the suction of the sample surface (200) may be disposed in the space (108) defined within the housing (202) at pre-defined positions. The pre-defined positions in the present disclosure may be at an angle of 120° apart from each of the suction units (103). However, this position should not be construed as a limitation as it may be arranged in other positions as well. The pre-defined positions of the suction unit (103) may aid in proper suction of the sample surface (200) i.e., the sample surface (200) may be uplifted uniformly or non-uniformly to get it in contact with the optical fibers (101) in the desired way. Also, this configuration may reduce air pockets that are likely to be caused during the examination of the sample surface (200) in conventional methods. In an embodiment, the activation and deactivation actuators may be selectively operated by the control unit (105) to exert variable suction pressure on the sample surface (200).

Figure 2A:
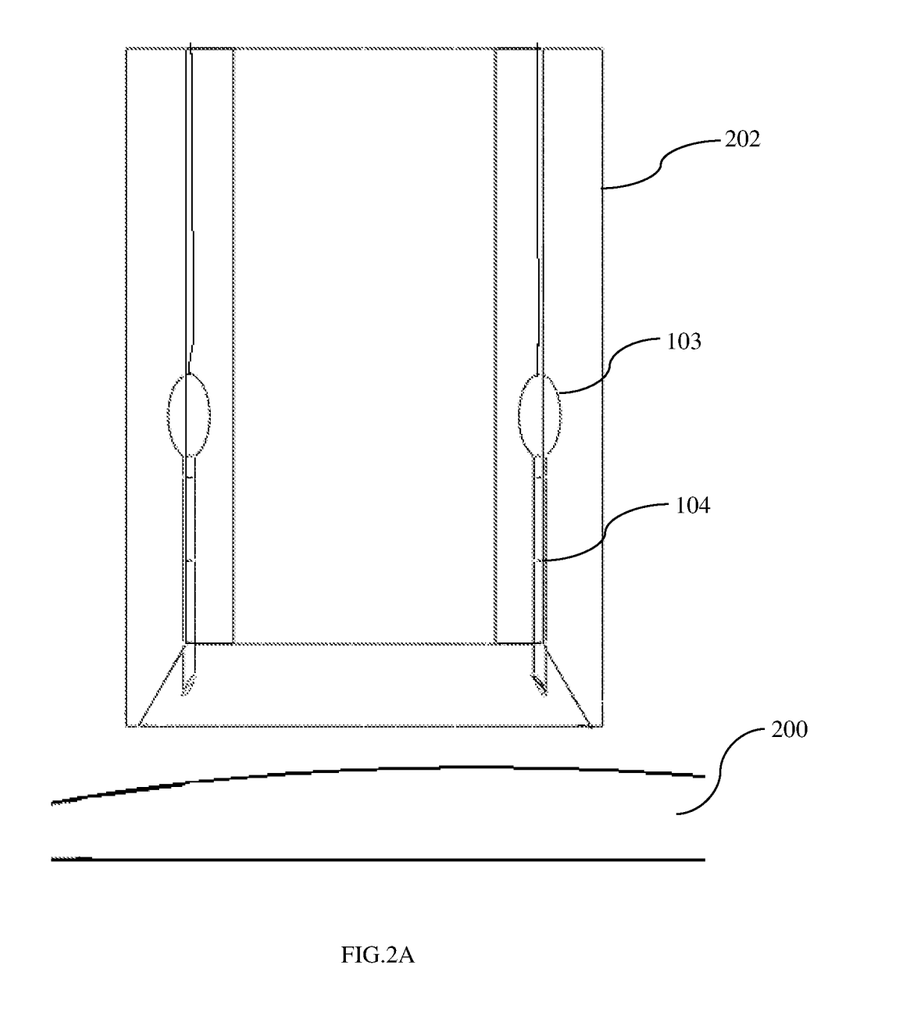
FIG. 2A is a front view of the mechanism of FIG. 1 when it is being placed on a surface of examination, in accordance with an embodiment of the disclosure.
Figure 2B:
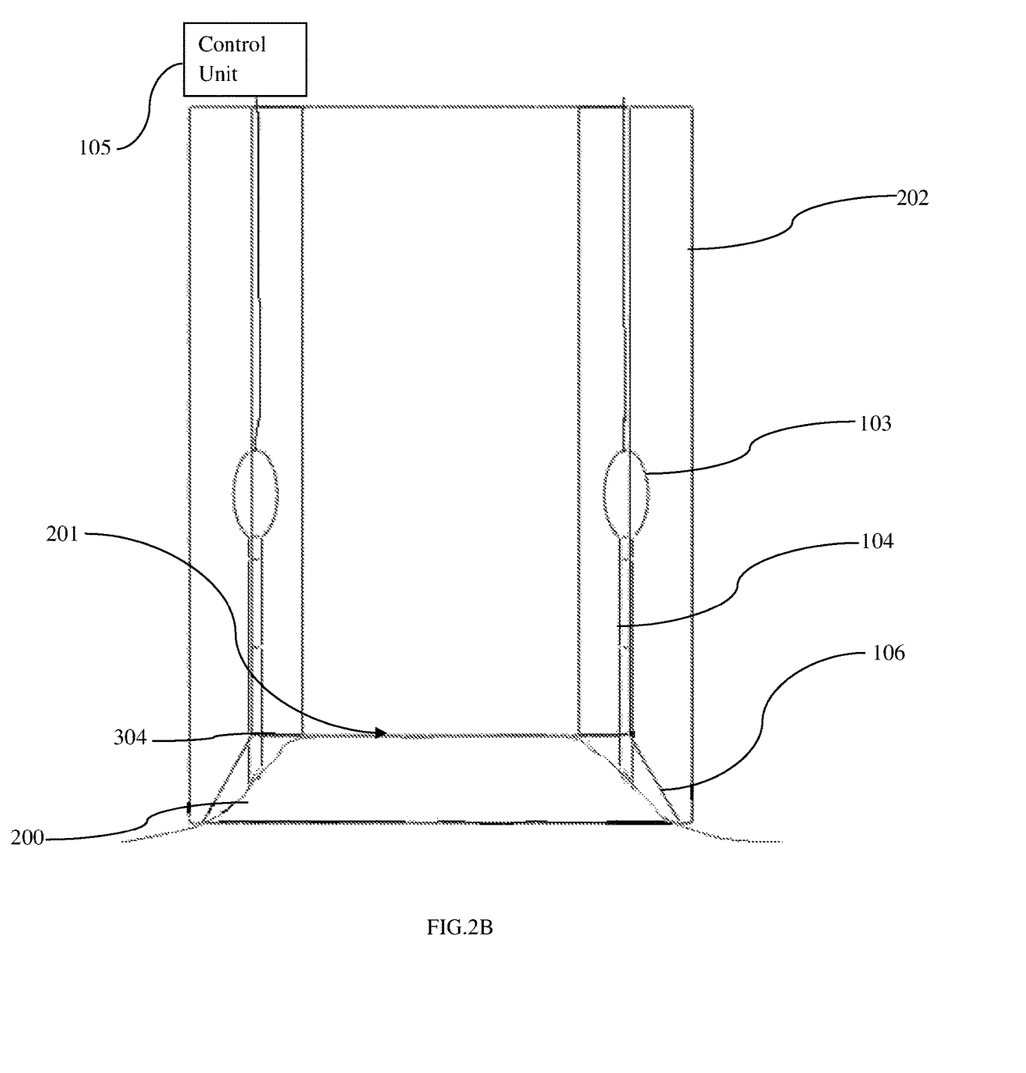
FIG. 2B is a front view of the mechanism of FIG. 1 when it is placed on a surface of examination, in accordance with an embodiment of the disclosure.

Moving on to FIG. 2A and FIG. 2B, it shows an exemplary embodiment of the present disclosure, when the guarding wall mechanism (100) is placed on a sample surface (200). FIG. 2A and FIG. 2B shows a detailed view of the working of the housing (202) in line with all other components of the guarding wall mechanism (100). The guarding wall mechanism (100) may be placed over the sample surface (200) (as shown in FIG. 2A). Due to the chamfer (106) provided in the guarding wall (100), when the housing (202) is placed over the sample surface (200), the surface (200) may be uplifted naturally to an extent. Further the suction units (103) provided in the guarding mechanism (100) aids the sample surface (200) to be further uplifted (as shown in FIG. 2B). Thus, a natural suction may be created with the provision of chamfer (106), and the sample surface (200) further advances into the cavity (107) through the suction units (103) ensuring that the surface (200) of the sample comes in contact with the free end (109) of the optical fiber (101) or much closer to it. The interface of the free end (109) of the optical fiber (101) and sample surface (200) is shown as 201 in FIG. 2. This contact ensure that, optical fiber (101) receives the complete signals from the sample surface (200), and also reduces the pressure that would act on the optical fibers (101) and limits damage.

Figure 3:
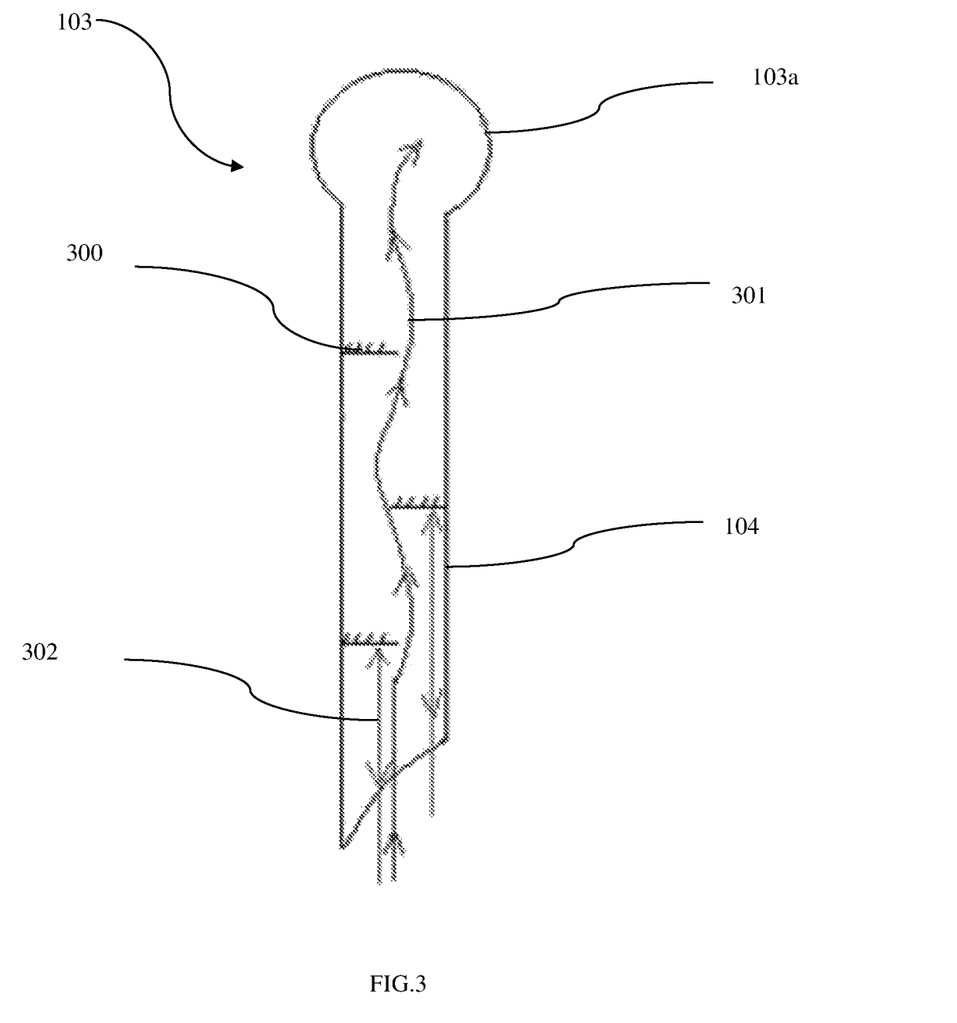
FIG. 3 is a schematic representation of a suction unit of the mechanism, depicting working of reflective plates housed in a suction tube and movement of air and light, in accordance with an embodiment of the disclosure.

Referring now to FIG. 3, the figure shows detailed view of the suction units (103), the suction units (103) includes a suction bulb (103a), a suction tube (104) and reflective plates (300). The suction bulb (103), as described earlier may be activated and deactivated through control unit (105). The control unit (105) may be configured to control the compression and expansion of the suction bulbs (103). This compression and expansion may be required in order to create a vacuum in the cavity (107) when the housing (202) is placed on the sample surface (200). The suction bulbs (103) may aid in the uplifting or suction of the sample surface (200) to bring it in contact with the optical fibers (101) (or closer to it). Further, the suction units (303) consists of a suction tube (104) which leads to have a connection between the suction bulb (103). The suction tube (104) houses a plurality of reflective plates (300) configured in it. The reflective plates (300) may be sized to cover only a part (say half) of the aperture of the suction tube (104) and are placed alternately on the opposite sides of the suction tube (104) in a configuration so as to cover the entire aperture or inner cross sectional area of the tube. the reflective plates or baffle plates may be placed in a different configuration than that to cover half of the aperture and on opposite sides but would collectively cover the whole (or majority) of the aperture. In an embodiment, the shape of the reflective plates may be at least one of but not limiting to a semicircular shape and can be shaped at any angle including but not limiting to 90°, 120° or 72°. The reflective plates (104) may reflect back the light that is emitted from the optical fiber (101) which may accidentally get reflected to the suction tubes (104). This helps in reduction of the light losses during the examination of the sample surface (200). Here we are taking advantage of light travelling in a straight line.

Figure 4:
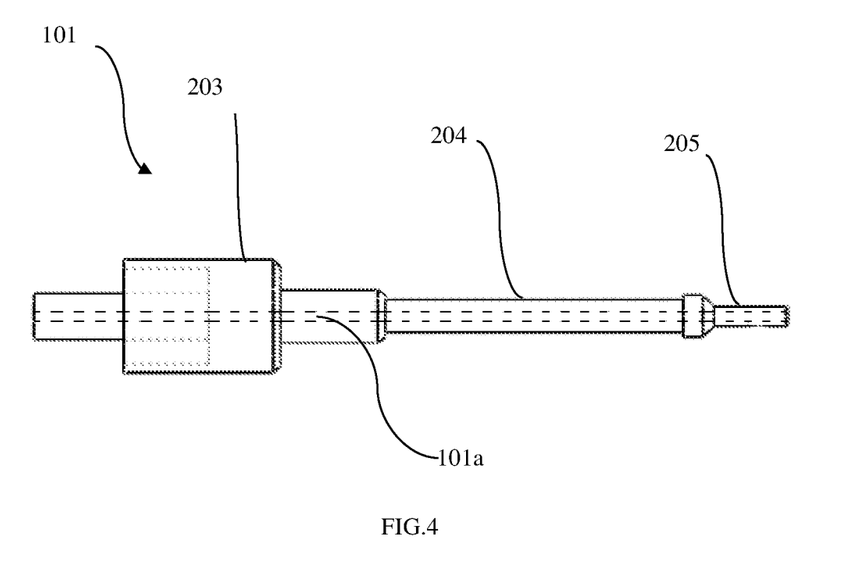
FIG. 4 is a schematic representation of an optical fiber, in accordance with an embodiment of the present disclosure.

Referring now to FIG. 4, which is a schematic representation of the optical fiber (101) which may be used in the guarding wall mechanism (100) of the present disclosure. The optical fiber (101) may include a connector portion (203), a body portion (204) and a ferrule (205). The connector portion (203) of the optical fiber (101) may be configured to connect a light source (not shown) of the optical system to the body portion (204) and the ferrule (205). In an embodiment, the connector portion (203) may be configured to efficiently transmit light between the light source to the free end (109) of the optical fiber (101). Further, one end of the body portion (204) may be coupled to the connector portion (203) and another end of the body portion (204) may be connected to the ferrule (205). In an embodiment, the body portion (204) may be made of at least one of a flexible material and a solid material. In some embodiments, the length of the optical fiber (101) may be determined based on the length of the body portion (204). Further, the ferrule (205) coupled to the body portion (204) may be configured to house the free end (109) of the optical fiber (101). In an embodiment, a core (101a) of the optical fiber (101) may run through or may pass through the connector portion (203), the body portion (204) and the ferrule (205), wherein the core (101a) is configured to carry optical signals/light from the light source to the free end (109) of the optical fiber (101).

In an embodiment, the guarding wall mechanism (100) of the present disclosure eliminates light leakage from the optical fiber (101) to the surroundings. Further, the guarding wall mechanism (100) ensures that there are minimal Fresnel losses in the optical system. Further, the guarding wall mechanism (100) increases comfort to the patient when it is positioned on the examination surface such as scalp or skin of the patient.

It may be noted that, one skilled in the art would modify the configuration of the guarding wall mechanism (100) to suit different packaging requirements without deviating from scope of the disclosure. Such modifications should be considered as a part of the present disclosure.

EQUIVALENTS

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding the description may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated in the description

| Table of Referral Numerals: | |
|---|---|
| Reference Number | Description |
| 100 | Guarding wall mechanism |
| 101 | Optical fibres |
| 101a | Core of the optical fibre |
| 102 | Cladding |
| 103 | Suction units |
| 103a | Suction bulb |
| 104 | Suction tube |
| 105 | Control unit |
| 106 | Chamfer |
| 107 | Cavity |
| 108 | Space |
| 109 | Free end of the optical fibre |
| 200 | Sample surface |
| 201 | Optical fibre and sample surface interface |
| 202 | Housing |
| 203 | Connector portion |
| 204 | Body |
| 205 | Ferrule |
| 206 | Proximal end |
| 207 | Distal end |
| 300 | Reflective plate |
| 301 | Passage of air to the suction bulb |
| 302 | Passage of light through the suction tube |
| 304 | Flange portion |

The invention claimed is:

1. A guarding wall mechanism for an optical fiber, the mechanism comprising:
a housing adapted to house the optical fiber, wherein the housing defines a space between the optical fiber and a guarding wall of the housing; and a plurality of suction units disposed in the space, wherein each of the plurality of suction units comprises a suction tube and a suction bulb, wherein, each of the plurality of suction units are configured to selectively exert at least one of even and uneven suction pressure on an examination surface to bring the examination surface in at least one of partial and complete contact with a free end of the optical fiber.

2. The mechanism as claimed in claim 1, wherein the housing is a hollow tube comprising an inner wall and an outer wall.

3. The mechanism as claimed in claim 1, wherein an end of the housing, proximal to the free end of the at least one optical fiber is defined with a chamfer.

4. The mechanism as claimed in claim 3, wherein the chamfer extends radially inward from the inner wall of the housing towards a substantially central portion of the housing up to a predetermined length, defining an opening at the substantially central portion of the housing.

5. The mechanism as claimed in claim 4 comprises a flange portion defined around the opening, wherein the flange portion is configured to support the free end of the optical fiber.

6. The mechanism as claimed in claim 1, wherein the housing is made of polymeric material.

7. The mechanism as claimed in claim 1, wherein the suction tube of each of the plurality of suction units extends from a cavity defined by the chamfer and the suction bulb is positioned at a free end of the suction tube.

8. The mechanism as claimed in claim 1 comprises a plurality of reflective plates provisioned within the suction units, wherein the plurality of reflective plates are configured to reflect light entering the plurality of suction units.

9. The mechanism as claimed in claim 1, wherein each of the plurality of suction units are coupled to an actuator.

10. The mechanism as claimed in claim 9, wherein the actuator is communicatively coupled to the control unit and the control unit is configured to selectively operate the actuator to activate and deactivate the plurality of suction units.

11. The guarding wall mechanism as claimed in claim 1, wherein the optical fiber housed within the housing is at least one of a transmitter optical fiber and a receiver optical fiber.

12. The guarding wall mechanism as claimed in claim 1, wherein the optical fiber includes a connector portion, a body portion and a ferrule.

13. The guarding wall mechanism as claimed in claim 11, wherein the connector portion is configured to facilitate transmission of light between at least one of a light source, a detector and the ferrule.

14. The guarding wall mechanism as claimed in claim 11, wherein the body of the optical fiber is configured to connect the ferrule of the optical fiber to the connector of the optical fiber and the body portion is made of at least one of a flexible material and a solid material.

15. The guarding wall mechanism as claimed in claim 11, wherein the ferrule includes the free end of the optical fiber and the ferrule is configured to support the free end of the optical fiber.

16. An optical system for examining a surface of a subject, the optical system comprising:
- at least one optical fiber, wherein the optical fiber comprises:
  - a ferrule including a free end of the optical fiber;
  - a connector portion configured to facilitate transmission of light between at least a light source, a detector and free end of the ferrule;
  - a body, wherein one end of the body is coupled to the ferrule and another end of the body is coupled to the connector;
  - a core of the optical fiber extends throughout the ferrule, body portion and the connector portion, wherein the core of the optical fiber is configured to transmit the light from the source to the examination surface; and
- a guarding wall mechanism for the at least one optical fiber, the mechanism comprising:
- a housing adapted to house the at least one optical fiber, wherein the housing defines a space between the optical fiber and a guarding wall of the housing and
- a plurality of suction units disposed in the hollow space wherein each of the plurality of suction units comprises a suction tube and a suction bulb, wherein, each of the plurality of suction units are configured to selectively exert suction pressure on an examination surface to bring the examination surface in contact with a free end of the optical fiber.

\* \* \* \* \*